United States Patent [19]

Muller

[11] Patent Number: 4,553,956
[45] Date of Patent: Nov. 19, 1985

[54] SHUNT VALVE AND METHOD OF USE

[75] Inventor: A. Bromley Muller, Kinnelon, N.J.

[73] Assignee: Becton, Dickinson and Co., Paramus, N.J.

[21] Appl. No.: 635,331

[22] Filed: Sep. 11, 1984

Related U.S. Application Data

[63] Continuation of Ser. No. 414,990, Sep. 3, 1982, Pat. No. 4,475,899.

[51] Int. Cl.⁴ ............................................. A61M 27/00
[52] U.S. Cl. ...................................................... 604/9
[58] Field of Search .................... 604/9, 8; 251/61.2, 251/61.1, 331; 137/528

[56] References Cited

U.S. PATENT DOCUMENTS

| | | | |
|---|---|---|---|
| 3,768,508 | 10/1973 | Schulte | 604/9 X |
| 3,886,948 | 6/1975 | Hakim | 604/9 |
| 3,910,283 | 10/1975 | Leveen | 604/9 |
| 4,332,255 | 6/1982 | Hakim et al. | 604/9 |

Primary Examiner—Stephen C. Pellegrino
Attorney, Agent, or Firm—John L. Voellmicke

[57] ABSTRACT

An operable shunt valve comprises a housing containing an inlet conduit for receiving fluid, an outlet conduit in fluid communication with the inlet conduit and a valve seat positioned between the inlet and the outlet conduits. A normally closed valve is movably positioned in the housing resting against the valve seat and adapted to move away from the valve seat in response to fluid pressure in the inlet conduit. A normally collapsed expansible balloon is positioned in the inlet conduit and, when expanded, adapted to contact the valve to lift the valve from the valve seat. A reservoir mechanism is provided for controllably and manually expanding the balloon to thereby force the valve open in the event the valve becomes unresponsive to fluid pressure in the inlet. A method of using an operable, implanted shunt valve, substantially as described above, is also within the purview of the present invention.

2 Claims, 9 Drawing Figures

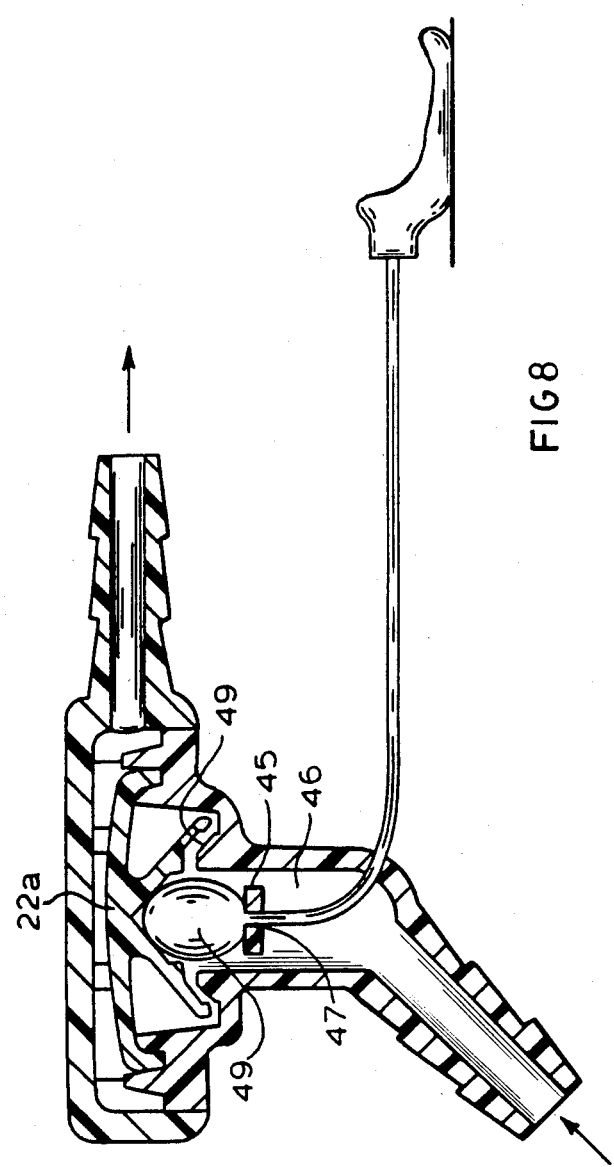

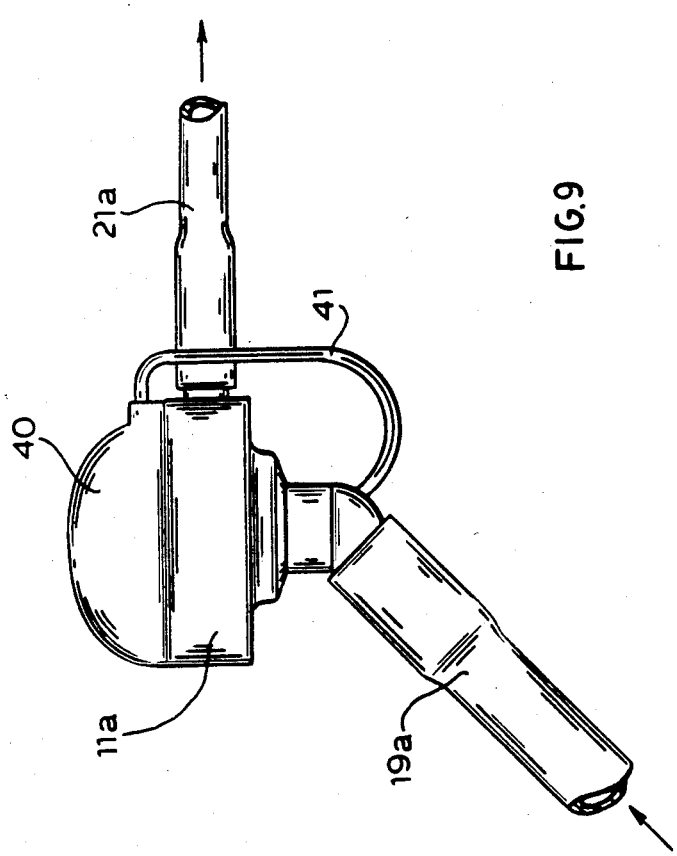

SHUNT VALVE AND METHOD OF USE

This is a continuation of application Ser. No. 414,990, filed Sept. 3, 1982, now U.S. Pat. No. 4,475,899.

FIELD OF THE INVENTION

The present invention relates to a shunt valve assembly with a clearing mechanism and a method for clearing the shunt valve in the event the valve becomes unresponsive to fluid pressure, and more particularly, concerns an implantable ascites shunt valve with a clearing mechanism used for transferring ascites fluid from the peritoneal cavity to the vascular system of a patient and a method for clearing the ascites shunt valve.

DESCRIPTION OF THE PRIOR ART

Certain physiological conditions, such as cirrhosis, cause the accumulation of ascites fluid in the peritoneal cavity. Continued accumulation can cause death. This condition can be relieved by surgically draining the peritoneal cavity. However, the ascites fluid is rich in protein and loss of these nutrients could lead to malnutrition.

The problems created by ascites fluid accumulation in the peritoneal cavity and the surgical relief of this accumulation were recognized by Dr. H. H. LeVeen who invented an implantable shunt valve assembly (U.S. Pat. No. 3,910,283) to allow ascites fluid, driven by pressure in the peritoneal cavity, to travel through a one-way valve to the patient's vascular system. The LeVeen invention uses a valve diaphragm which allows flow of ascites fluid to the vascular system when the intraperitoneal pressure exceeds the central venous pressure by a predetermined amount.

It is also possible that deposits such as precipitate of salts or other substances from the ascites fluid may, in time, build up so as to render the valve inoperable. This problem was recognized by J. B. Newkirk, patentee of a shunt valve assembly (U.S. Pat. No. 4,240,434) with an asymmetrical one-way duck-bill valve contained in a flexible pump body. U.S. Pat. No. 4,240,434 teaches that the asymmetrical properties of the valve make it self-cleaning and that squeezing the pump body, which is positioned such that ascites fluid enters it after leaving the duck-bill valve, further clears the valve. However, the Newkirk apparatus relies upon fluid pressure built up by squeezing action of the pump, rather than direct physical contact to force the valve open. This squeezing action causes fluid to be forced out of the valve system. When the shunt valve communicates with the venous system there is a possibility that blood will clot at the end of the tube in contact with the blood supply. The fluid being forced out of the shunt valve system can potentially dislodge a blood clot that may have formed at the end of the outlet tube, and set it free in the circulatory system where it can potentially harm the patient. In addition, Newkirk's design requires that the shunt valve be placed at the same location as the means for activating the clearing mechanism. There is a risk of crushing or damaging the valve or breaking cemented joints when applying pressure to a pump body which contains the shunt valve. Also, failure of the pump body could lead to blood escaping the venous system.

With the above-mentioned deficiencies in mind it is desired to provide, in particular, an ascites shunt valve with a means and a method for forcing the valve open in the event it becomes unresponsive to the pressures exerted by the ascites fluid. It is desired to provide a clearing mechanism that does not force fluid into the venous system since this fluid may dislodge particles on the surface of the outlet tube and set them free in the patient's circulatory system. It is further desired to provide a clearing mechanism preferably contained in a separate system so that the components of the shunt valve are not exposed to the forces required to activate the clearing mechanism and that unexpected failure of the clearing mechanism will not result in failure of the integrity of the fluid path of the ascites fluid from the peritoneal cavity to the vascular system. It is also desired to have a clearing mechanism that need not be placed at the same location as the shunt valve.

SUMMARY OF THE INVENTION

The shunt valve of the present invention comprises a housing containing inlet means, outlet means and normally closed valve means responsive to fluid pressure in the inlet means for allowing fluid flow between the inlet means and the outlet means. Externally activated means is provided for controllably contacting and forcing the valve means into an open position to assure fluid flow between the inlet means and the outlet means in the event the valve means is unresponsive to fluid pressure in the inlet means.

In a preferred embodiment of one aspect of the present invention an operable implantable ascites shunt valve includes a housing which contains an inlet conduit for receiving ascites fluid from the peritoneal cavity of the patient and an outlet conduit in fluid communication with the inlet conduit for delivering ascites fluid into the vascular system of the patient. A valve seat is positioned intermediate the inlet conduit and the outlet conduit, and a normally closed valve diaphragm is movably positioned in the housing resting against the valve seat. The valve diaphragm is adapted to move away from the valve seat in response to fluid pressure in the inlet conduit to allow ascites fluid flow between the inlet conduit and the outlet conduit. A normally collapsed expansible balloon is positioned in the inlet conduit. When the balloon is expanded it occludes the inlet conduit thus preventing ascites fluid from reaching the valve diaphragm; further it contacts the valve diaphragm to lift it from the valve seat. A flexible tube is connected at one end to, and is in fluid communication with, the balloon. The tube exits the housing through a fluid-tight orifice in the inlet conduit and is connected at its other end to a flexible, normally expanded reservoir. A quantity of fluid fills the volume described by, and is transferable among, the reservoir, tube and balloon. When the reservoir is implanted in the patient it is subcutaneously accessible to the patient. In the event that the valve diaphragm is unresponsive to fluid pressure in the inlet conduit the patient may restore fluid flow between the inlet conduit and the outlet conduit by compressing the reservoir with sufficient force to collapse the reservoir and expand the balloon whereby the balloon in its expanded position occludes the inlet conduit and lifts the valve diaphram from the valve seat.

Another aspect of the present invention is a method of clearing a valve implanted in an animal body. The implanted valve has a housing containing inlet means, outlet means and normally closed valve means responsive to fluid pressure in the inlet means, and includes controllable clearing means for contacting and forcing the valve means into an open position. In accordance with the invention, the method comprises activating the clearing means in the event that the valve means is unresponsive to fluid pressure in the inlet means thereby restoring fluid flow between the inlet means and the outlet means.

In accordance with the principles of the present invention a number of advantages and objectives are achieved. Primarily, the present invention provides an ascites shunt valve with a clearing mechanism for forcing the valve open in the event it becomes unresponsive to the pressures exerted by the ascites fluid. The present invention provides a clearing mechanism that does not force fluid through the shunt valve system where it can dislodge particles on the surface of the outlet tube and set them free in the patient's circulatory system. The present invention also provides a clearing mechanism that is preferably contained in a separate system from the shunt valve system that transports the ascites fluid from the peritoneal cavity to the vascular system. Therefore, the present invention offers the advantage of protecting the preferred valve diaphragm from the forces used to activate the clearing mechanism even if the housing and the reservoir are in close proximity to each other. A further advantage provided by the separate systems of the present invention is that uexpected failure of the balloon, tube or reservoir will not allow ascites fluid or blood to escape from the system. Finally, the present invention allows positioning of the reservoir in a different location from the shunt valve. This may be done in order to optimize the flow path of the ascites fluid or to accommodate special situations regarding the patient.

BRIEF DESCRIPTION OF THE DRAWINGS

FIG. 8 is an enlarged cross-sectional view of an alternative embodiment of the ascites shunt valve of the present invention; and FIG. 9 is a side elevational view of an alternative embodiment of the ascites shunt valve of the present invention.

DETAILED DESCRIPTION

Figure 1:
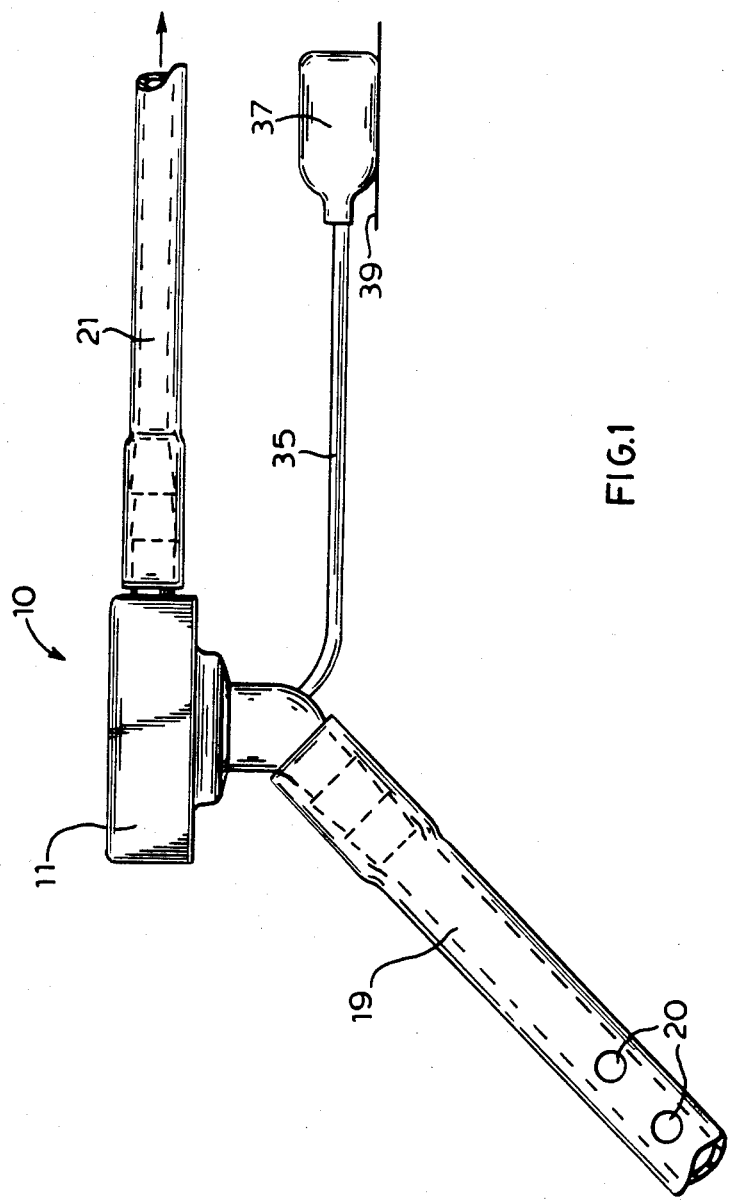
FIG. 1 is a side elevational view of the preferred implantable ascites shunt valve of the present invention.
Figure 2:
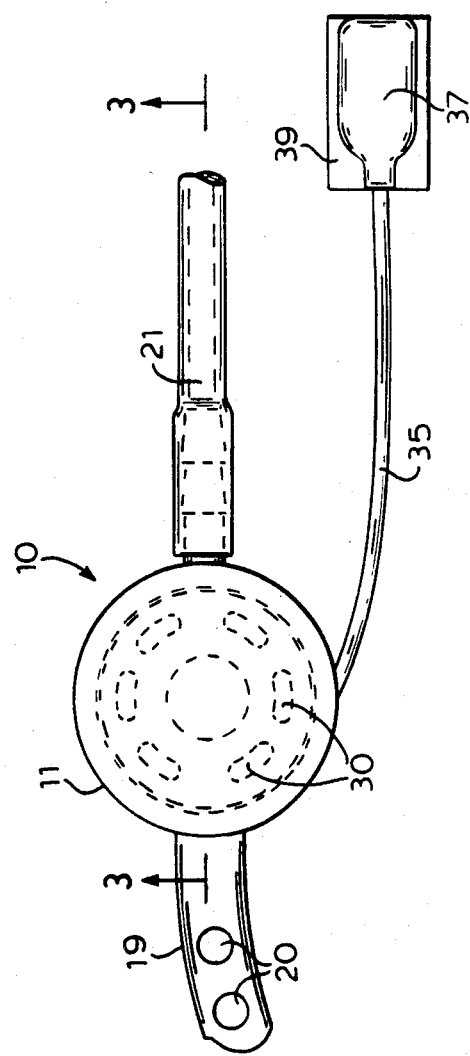
FIG. 2 is a top elevational view of the preferred implantable ascites shunt valve of the present invention.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Turning to FIGS. 1 through 5, an operable ascites shunt valve assembly 10 includes a housing 11 with an upper portion 12 and a lower portion 14 and a cavity 13 formed by the upper and lower portions. The housing contains an inlet conduit 15 preferably for receiving ascites fluid from the peritoneal cavity and an outlet conduit 16 in fluid communication with the inlet conduit. A circular valve seat 17 is located in the fluid path between the inlet and outlet conduits. In the embodiment shown, the inlet conduit has an angular displacement with respect to the outlet conduit. However, it is within the purview of this invention that the exterior of the housing can assume a variety of shapes and that the angles, if any, of the inlet and the outlet conduits relative to each other and to the housing can vary to accommodate different possible implant locations of the housing.

A flexible inlet tube 19 preferably with perforations 20, is connected to the inlet conduit and a flexible outlet tube 21 is connected to the outlet conduit. When implanted in the human body, inlet tube 19 communicates with the peritoneum. Perforations 20 facilitate entry of ascites fluid into the inlet tube. Outlet tube 21 is inserted into a large jugular vein or other large vein for passage of fluid into the vascular system.

A normally closed valve diaphragm 22 is movably positioned in the housing and rests against circular valve seat 17. In the preferred embodiment the valve diaphragm consists of an inverted cup-shaped sealing skirt 24 sized and shaped to fit the circular valve seat, a central connecting member 25 which is located between the sealing skirt and four radial struts 26 and peripheral support ring 27 connected to the radial struts. The peripheral support ring is positioned in a circular positioning slot 29 in the lower portion of the housing and it is held in this position by six locking lugs 30 which are an integral part of the upper portion of the housing. Valve diaphragm 22 is adapted to move away from the valve seat in response to fluid pressure in the inlet conduit to allow fluid flow from the open valve through spaces 31, between radial struts 26, and to the outlet conduit. When the pressure of the ascites fluid in the peritoneum exceeds the central venous pressure by a predetermined amount the valve diaphragm is forced open and ascites fluid flows through the housing to the vascular system. It is preferred that the valve diaphragm open when the ascites fluid pressure is approximately 3 cm $H_2O$ greater than the central venus pressures. A description of the shunt valve thus far is similar to that found in U.S. Pat. No. 3,910,283.

Figure 3:
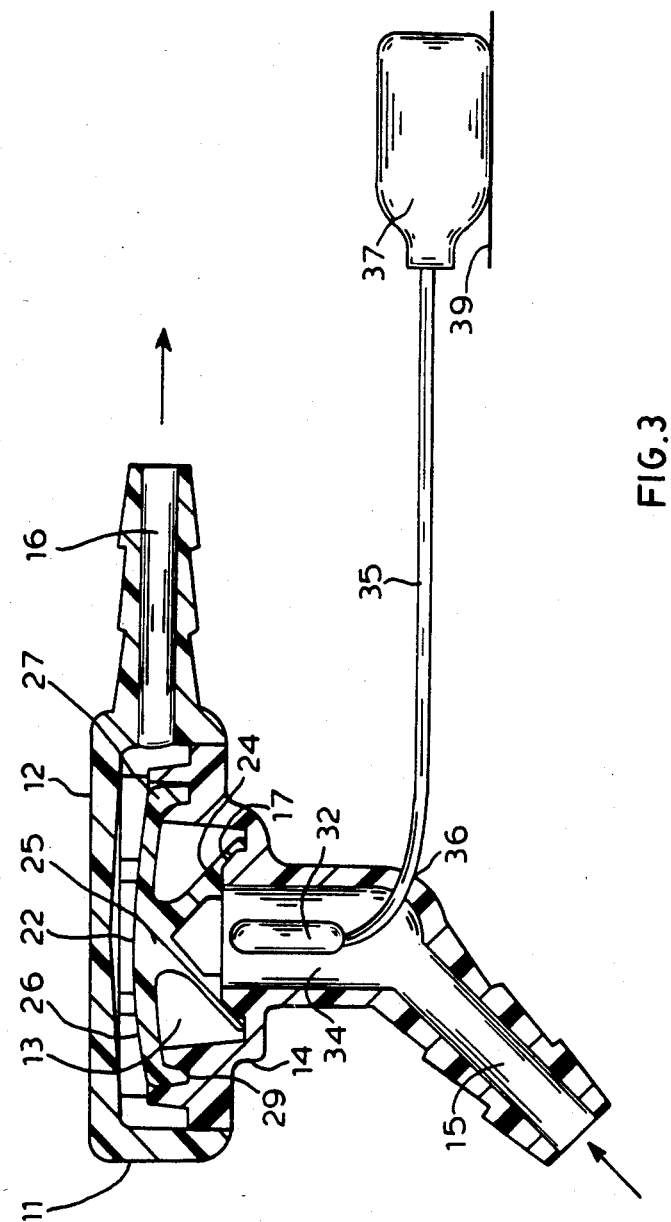
FIG. 3 is an enlarged cross-sectional view of the ascites shunt valve of FIG. 2 along line 3—3 illustrated without inlet and outlet tubes and showing the balloon in its normally collapsed position.
Figure 4:
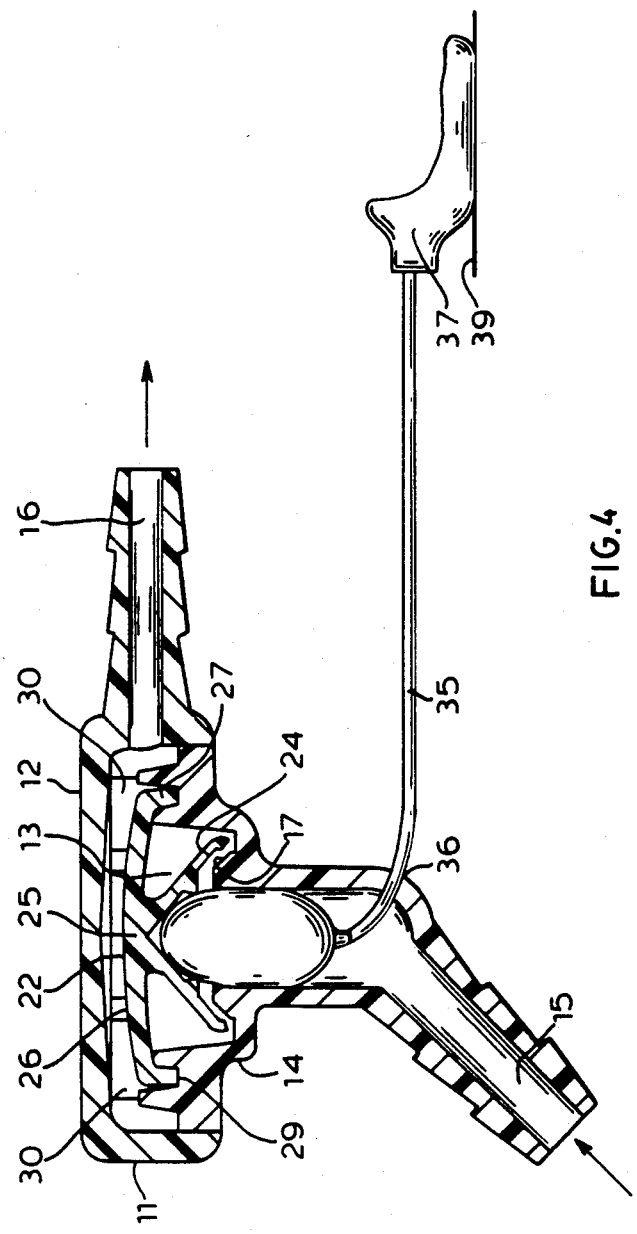
FIG. 4 is an enlarged cross-sectional view of the ascites shunt valve of FIG. 2 illustrated without inlet and outlet tubes and showing the balloon in the expanded position.

A normally collapsed expansible balloon 32 is positioned in an expanded portion 34 of the inlet conduit. The balloon is designed such that, when expanded, it preferably occludes the inlet conduit preventing further ascites fluid from reaching the valve diaphragm, and it contacts the valve diaphragm to lift same from valve seat 17. A flexible tube 35 is connected at one end and is in fluid communication with the balloon. Tube 35 exits the lower portion of the housing through a fluid tight orifice 36. In the preferred embodiment, an adhesive is used to completely seal orifice 36 after tube 35 is positioned in the orifice and to secure tube 35 so that it cannot move relative to orifice 36. The position of orifice 36 and the length of tube 35 positioned in expanded portion 34 should be chosen to position the balloon approximately as shown in FIG. 3. The other end of tube 35 is connected to and is in fluid communication with a normally expanded flexible reservoir 37. The reservoir when expanded preferably has an interior volume that is larger than the interior volume of the balloon when the balloon is expanded. A quantity of fluid fills the volume described by the balloon, tube and reservoir whereby compression of the reservoir is adapted to expand the balloon due to the transfer of fluid from the reservoir, through the tube and to the balloon.

Figure 7:
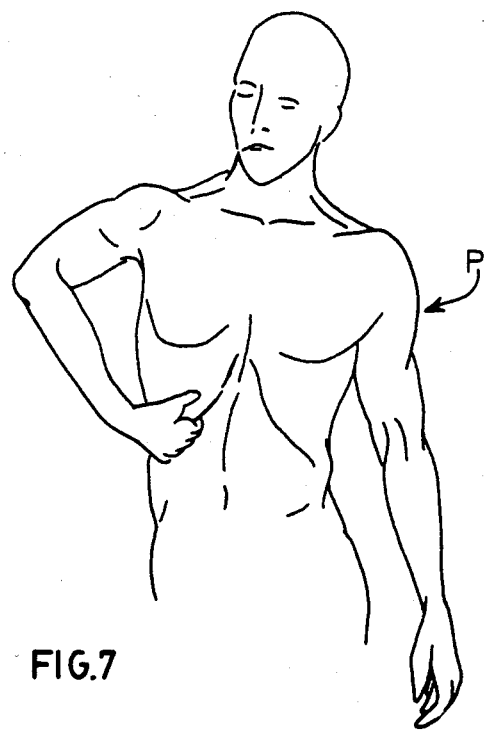
FIG. 7 is a perspective view showing the patient applying digital pressure to compress the reservoir mounted to the lower portion of the patient's rib cage.
Figure 5:
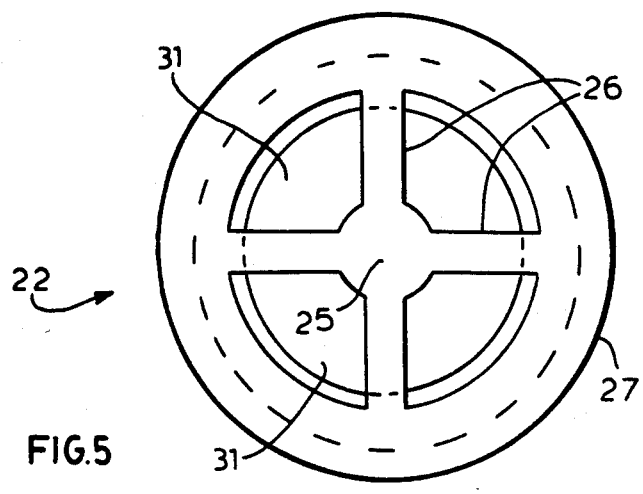
FIG. 5 is an enlarged top elevation view of the valve diaphragm.
Figure 6:
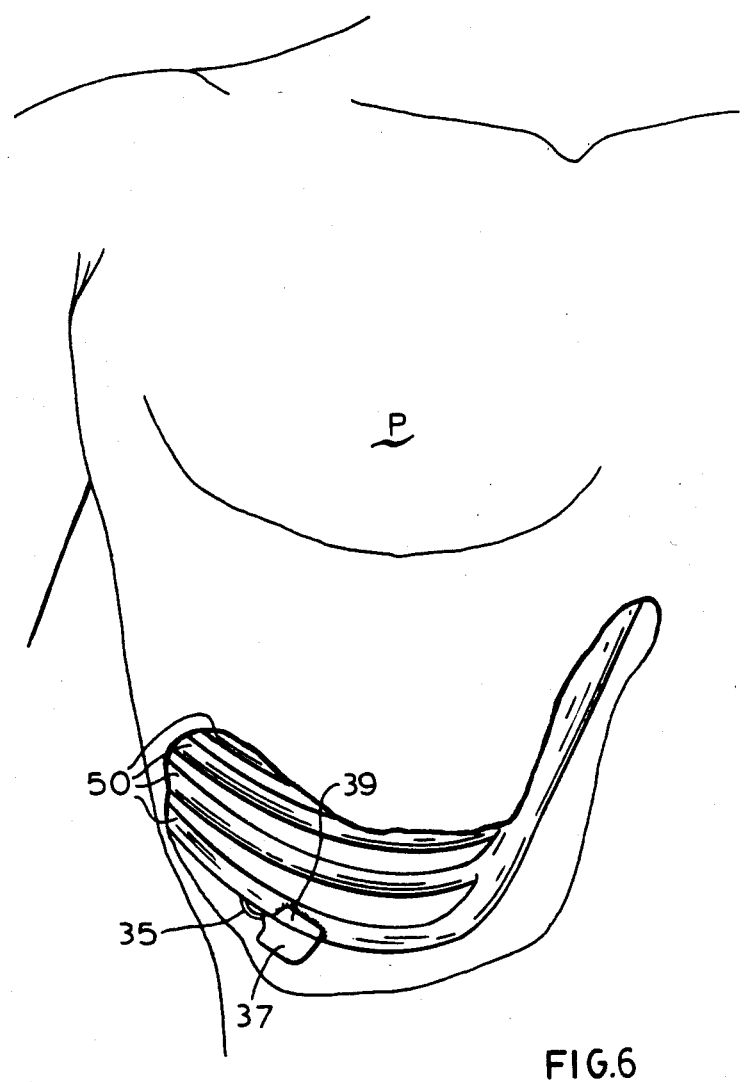
FIG. 6 is a perspective view showing the reservoir attached to the lower portion of the patient's rib cage.

Turning now to FIGS. 6 and 7, reservoir 29 is implanted in the patient P such that it is subcutaneously accessible. One possible area for implanting the reservoir would be adjacent to the rib cage 50 since the ribs provide a firm backing to maintain the position of the reservoir when finger pressure is applied to it. If sutures are used to position the reservoir it is desirable to provide additional material 39 which can be an integral part of reservoir 37 or a separate sheet of material such as polyester reinforced plastic or silicone rubber which is mounted on the reservoir. Although sutures may puncture or damage reservoir 37, additional material 39 can be sutured to the patient to fixedly contain the reservoir in the desired location.

The present invention, as illustrated in the drawings, provides a method for clearing an implanted ascites shunt valve. In use, the ascites shunt valve assembly is implanted in the patient such that inlet tube 19 communicates with the peritoneal cavity, outlet tube 20 is inserted into a large jugular vein or other large vein and reservoir 37 is positioned to be subcutaneously accessible, as shown in FIG. 6. In the event that the valve diaphragm becomes unresponsive to ascites fluid pressure in the inlet conduit, fluid flow between the inlet conduit and the outlet conduit may be restored by compressing reservoir 37, as shown in FIG. 7, with sufficient externally applied manual pressure to collapse the reservoir and expand balloon 32 whereby the balloon in its expanded position occludes the inlet conduit and contacts valve diaphragm 22 to lift same from valve seat 17. The pressure on the reservoir is then released thereby allowing the fluid to return from the balloon to the reservoir; thus the reservoir and the balloon expand and collapse, respectively, to their original positions.

FIG. 8 shows an alternative embodiment of the present invention. This embodiment is similar to the previously described embodiment except that a normally collapsed balloon 44, shown expanded, is held in position by a transverse support member 45 positioned in an inlet conduit 46. The balloon is designed such that, when expanded, it contacts a normally closed valve diaphragm 22a and lifts the valve diaphragm from a valve seat 49. It is preferred that balloon 44 be held in an aperture 47 in the transverse support member by the use of adhesive. The transverse support member may be a separate member attached to the interior surface of the inlet conduit or it may be an integral part of the housing. It should be noted that it is within the purview of this invention for the balloon or other like expansible members to be expanded to lift the valve diaphragm from the valve seat through the use of mechanical force rather than fluid pressure. This mechanical force may be provided, for instance, by the use of a flexible guide wire contained within a flexible tube. A balloon or a bellows enclosure may be connected to each end of the flexible tube and guide wire assembly such that force exerted on one flexible enclosure will force the guide wire along the closely fitting flexible tube causing the second flexible enclosure inside the housing to expand and lift the valve diaphragm from the valve seat. Other modifications of the embodiments as described herein are clearly within the scope of and spirit of the instant invention.

FIG. 9 shows an alternative embodiment wherein a reservoir 40 is connected to housing 11a. A tube 41 is connected to and in fluid communication with reservoir 40 at one end and is connected to and in fluid communication with the balloon (not shown) at the other end. In this embodiment when the reservoir is compressed to activate the clearing mechanism it is compressed against the housing rather than against a part of the patient's anatomy. The shunt valve of this embodiment must also be mounted in the patient so that the reservoir is subcutaneously accessible to external digital manipulation. Additional material, such as polyester reinforced plastic or silicone rubber may be connected to the housing to provide structure to suture the shunt valve in the desired position in the patient's body. It should be pointed out that even in this alternative embodiment the present invention offers the advantage that the valve diaphragm is protected from the manual force used to activate the clearing mechanism.

Although inlet tube 19 and outlet tube 21 may be made of many different materials, medical grade silicone rubber is preferred. Balloon 32, tube 35, reservoir 37 and valve diaphragm 22 are preferably made of medical grade silicone rubber. It is preferred that upper portion 12 and lower portion 14 of the housing be made of a rigid plastic, such as polypropylene. The upper and lower housing portions are preferably held together with an adhesive suitable for the type of plastic chosen or by using an ultrasonic welding process. Tube 35 may be connected at one end to balloon 32 and at the other end to reservoir 37 with adhesive. Also, adhesive may be used to position tube 35 in orifice 36 and to seal this connection. Silicone oil is the preferred fluid for filling the volume described by the balloon, tube and reservoir. Since the ascites shunt valve of this invention is preferably sterile when implanted in the patient all materials should be chosen to accommodate the sterilization process.

Thus, there has been provided in accordance with the present invention an ascites shunt, or like, valve with a clearing mechanism for forcing the valve diaphragm open in the event it becomes unresponsive to the pressures exerted by fluid in the inlet.

What is claimed is:
1. An operable implantable ascites shunt valve comprising:
   a housing containing a valve seat, inlet means for receiving ascites fluid from the peritoneal cavity and outlet means;
   normally closed valve means movably positioned in said housing resting against said valve seat and responsive to fluid pressure in said inlet means for allowing fluid flow between said inlet means and said outlet means; and
   manually activatable means for controllably contacting and forcing said valve means from said valve seat into an open position to assure fluid flow between said inlet means and said outlet means in the event said valve means is unresponsive to fluid pressure in said inlet means, said manually activatable means allowing manual activation at a location removed from said housing.

2. A method of clearing an ascites shunt valve, implanted in an animal body, of the type having a housing containing a valve seat, inlet means for receiving ascites fluid from the peritoneal cavity, outlet means and normally closed valve means movably positioned in said housing resting against said valve seat and responsive to fluid pressure in the inlet means for allowing fluid flow between the inlet means and the outlet means, the valve including controllable clearing means, manually activatable at a location removed from said housing, for contacting and forcing the valve means from said valve seat into an open position comprising:

manipulatively activating the clearing means in the event that the valve means is unresponsive to fluid pressure in the inlet means thereby restoring fluid flow between the inlet means and the outlet means.

\* \* \* \* \*